(12) United States Patent
Martin (10) Patent No.: US 9,566,407 B2
(45) Date of Patent: *Feb. 14, 2017

(54) NASAL CANNULA ASSEMBLY WITH FLOW CONTROL PASSAGE COMMUNICATING WITH A DEFORMABLE RESERVOIR

(71) Applicant: L'Air Liquide, Société Anonyme pour l'Etude et l'Exploitation des Procédés Georges Claude, Paris (FR)

(72) Inventor: Andrew Martin, Wilmington, DE (US)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 564 days.

This patent is subject to a terminal disclaimer.

(21) Appl. No.: 13/930,460

(22) Filed: Jun. 28, 2013

(65) Prior Publication Data

US 2015/0000660 A1  Jan. 1, 2015

(51) Int. Cl.
*A61M 16/06* (2006.01)
*A61M 16/10* (2006.01)
(Continued)

(52) U.S. Cl.
CPC ..... *A61M 16/0672* (2014.02); *A61M 16/0666* (2013.01); *A61M 16/0866* (2014.02);
(Continued)

(58) Field of Classification Search
CPC .............. A61M 16/00; A61M 16/0443; A61M 16/0461; A61M 16/06; A61M 16/0616; A61M 16/0622; A61M 16/0633; A61M 16/0666; A61M 16/0672; A61M 16/0677; A61M 16/0683; A61M 16/0866; A61M 16/10; A61M 16/1005; A61M 16/104; A61M 16/1045; A61M 16/12; A61M 16/122; A61M 16/125; A61M 16/20; A61M 16/208; A61M 15/0088; A61M 15/08; A61M 2016/0661
(Continued)

(56) References Cited

U.S. PATENT DOCUMENTS 2,535,938 A    12/1950  Lombard
2,843,119 A *   7/1958  Glasser .................... A61D 7/04
                                                 128/205.17
(Continued)

FOREIGN PATENT DOCUMENTS

EP    0 010 880      5/1980
EP    1 516 639      3/2005
(Continued)

OTHER PUBLICATIONS

"Ambu® SPUR® II" spec sheet; retrieved from http://www.ambu.com/corp/products/anaesthesia/product/spur%C2%AE_ii_-_disposable_resuscitator-prod14586.aspx.*
(Continued)

*Primary Examiner* — Tan-Uyen (Jackie) T Ho
*Assistant Examiner* — Joseph D Boecker
(74) *Attorney, Agent, or Firm* — Allen E. White (57) ABSTRACT

The invention concerns a nasal cannula assembly (10) adapted to deliver gases to a patient comprising a first compartment (1) and a second compartment (2) separated by a separation wall (6); a pair of nasal prongs (5) in fluid communication with the first compartment (1); the first compartment (1) comprising a first inlet (11) for introducing a first gas into said first compartment (1); the second compartment (2) comprising a second inlet (2) for introducing a second gas into said second compartment (2); and the separation wall (6) comprising at least one flow restriction
(Continued)

element (35) for controlling the passage of gas from the second compartment (2) to the first compartment (1).

2 Claims, 9 Drawing Sheets (51) Int. Cl.
*A61M 16/12* (2006.01)
*A61M 16/20* (2006.01)
*A61M 16/08* (2006.01)

(52) U.S. Cl.
CPC ......... *A61M 16/122* (2014.02); *A61M 16/125* (2014.02); *A61M 16/208* (2013.01); *A61M 2202/0208* (2013.01); *A61M 2202/0275* (2013.01); *A61M 2209/02* (2013.01)

(58) Field of Classification Search
USPC ............ 128/200.24, 200.26, 203.12, 203.13, 128/203.22, 203.25, 204.12, 204.18, 128/205.11, 205.14, 205.25, 206.11, 128/206.12, 206.13, 206.18, 206.27, 128/207.11, 207.13, 207.18; 604/164.11, 264, 537, 539, 912
See application file for complete search history.

(56) References Cited

U.S. PATENT DOCUMENTS

| | | | |
|---|---|---|---|
| 3,513,844 A | 5/1970 | Smith | |
| 4,434,797 A * | 3/1984 | Silander | A61F 2/94 604/264 |
| 4,492,228 A * | 1/1985 | Makovic | A61M 16/1075 128/207.17 |
| 4,535,767 A | 8/1985 | Tiep et al. | |
| 4,989,599 A * | 2/1991 | Carter | A61M 16/0666 128/204.18 |
| 5,286,739 A | 2/1994 | Kilbourn et al. | |
| 5,477,852 A * | 12/1995 | Landis | A61M 16/0633 128/204.18 |
| 5,558,083 A | 9/1996 | Bathe et al. | |
| 5,732,693 A | 3/1998 | Bathe et al. | |
| 5,873,359 A | 2/1999 | Zapol et al. | |
| 6,016,802 A * | 1/2000 | Jackson | A62B 9/02 128/201.19 |
| 6,033,379 A * | 3/2000 | Barra | A61M 25/10 604/103.11 |
| 6,051,241 A | 4/2000 | Briend et al. | |
| 6,089,229 A | 7/2000 | Bathe et al. | |
| 6,142,147 A | 11/2000 | Head et al. | |
| 6,431,172 B1 * | 8/2002 | Bordewick | A61M 16/0666 128/206.11 |
| 6,478,026 B1 * | 11/2002 | Wood | A61M 16/0666 128/207.13 |
| 6,581,599 B1 | 6/2003 | Stenzler | |
| 6,644,315 B2 | 11/2003 | Ziaee | |
| 6,668,828 B1 | 12/2003 | Figley et al. | |
| 6,799,575 B1 * | 10/2004 | Carter | A61M 16/0666 128/204.18 |
| 7,328,703 B1 * | 2/2008 | Tiep | A61M 16/0666 128/204.24 |
| 7,481,219 B2 * | 1/2009 | Lewis | A61D 7/04 128/206.11 |
| 8,979,810 B1 * | 3/2015 | Beyer | A61M 1/0023 604/173 |
| 2001/0019034 A1 | 9/2001 | Tai et al. | |
| 2002/0017300 A1 * | 2/2002 | Hickle | A61B 5/0836 128/204.22 |
| 2002/0078952 A1 * | 6/2002 | Hopper | A61F 11/00 128/200.24 |
| 2003/0150458 A1 * | 8/2003 | Arnott | A61M 16/06 128/204.18 |
| 2004/0040558 A1 * | 3/2004 | Psaros | A61M 15/0028 128/204.18 |
| 2004/0163647 A1 * | 8/2004 | Figley | A61M 16/00 128/204.18 |
| 2006/0107958 A1 * | 5/2006 | Sleeper | A61M 16/0666 128/206.11 |
| 2006/0266361 A1 * | 11/2006 | Hernandez | A61M 16/06 128/206.11 |
| 2008/0041393 A1 * | 2/2008 | Bracken | A61M 16/0666 128/207.18 |
| 2008/0047559 A1 * | 2/2008 | Fiori | A61M 16/0666 128/206.11 |
| 2008/0142012 A1 * | 6/2008 | Farnsworth | A61M 16/00 128/205.24 |
| 2008/0142013 A1 * | 6/2008 | Hallett | A61M 16/06 128/205.24 |
| 2009/0101147 A1 * | 4/2009 | Landis | A61M 16/0666 128/204.18 |
| 2009/0260628 A1 * | 10/2009 | Flynn, Sr. | A61M 16/0078 128/203.28 |
| 2011/0094518 A1 * | 4/2011 | Cipollone | A61M 16/0666 128/207.18 |
| 2011/0108041 A1 * | 5/2011 | Sather | A61M 15/08 128/848 |
| 2011/0240035 A1 * | 10/2011 | Gillies | A61M 16/0666 128/207.18 |
| 2011/0284001 A1 * | 11/2011 | Tero | A61M 16/0666 128/204.18 |
| 2012/0305001 A1 * | 12/2012 | Tatkov | A61M 16/06 128/205.25 |
| 2013/0211275 A1 * | 8/2013 | Curti | A61M 16/0666 600/543 |
| 2013/0245483 A1 * | 9/2013 | Eichler | A61B 5/082 600/532 |
| 2014/0066801 A1 * | 3/2014 | Tero | A61M 16/0666 600/543 |
| 2014/0130805 A1 * | 5/2014 | Tiep | A61M 16/0672 128/207.18 |
| 2014/0150789 A1 * | 6/2014 | Flanagan | A61M 16/0672 128/203.22 |
| 2014/0166009 A1 * | 6/2014 | Flanagan | A61M 16/0677 128/203.22 |
| 2016/0030229 A1 * | 2/2016 | Goldschmidt | A61F 5/56 128/847 |

FOREIGN PATENT DOCUMENTS

| | | |
|---|---|---|
| GB | 2 493 520 | 2/2013 |
| WO | WO 2005 099801 | 10/2005 |
| WO | WO 2010 076711 | 7/2010 |

OTHER PUBLICATIONS

Partial International Search Report for related PCT/US2014/044494, Oct. 2, 2014.

Dumont, C.P. et al., "Using a reservoir nasal cannula in acute care," Critical Care Nurse, vol. 22, No. 4, Aug. 2002, pp. 41-46.

* cited by examiner

Flow (top) and pressure (bottom) versus time waveforms obtained from the lung simulator with no filter. The X-axis units are seconds, while the Y-axis units are L/min and cm $H_2O$, respectively.

NASAL CANNULA ASSEMBLY WITH FLOW CONTROL PASSAGE COMMUNICATING WITH A DEFORMABLE RESERVOIR

BACKGROUND OF THE INVENTION

Field of the Invention

The invention concerns a nasal cannula assembly adapted to deliver gases to a patient, especially for NO gas therapy, a breathing assistance apparatus comprising such a nasal cannula assembly, and a method for treating pulmonary vasoconstriction in a patient using such a nasal cannula assembly and/or breathing assistance apparatus.

Description of the State of the Art

NO/nitrogen gas mixtures are commonly used for treating vasoconstrictions of the lung and pulmonary hypertension in adults and infants.

For instance, EP-A-1516639 discloses a gaseous mixture consisting of NO and an inert gas, preferably nitrogen, used for the production of an inhalable medicament for treating persistent pulmonary hypertension of the newborn.

Before being inhaled by the patient, the $NO/N_2$ mixture is generally diluted in an oxygen-containing gas, such as air or a $O_2/N_2$ mixture, comprising at least 21 vol. % of oxygen.

Typically, NO is present in the final mixture in an amount of several (1-800, most often 5-80) ppm in volume.

However, as NO is rapidly oxidized into $NO_2$ in the presence of oxygen, it is important to avoid long residence times in gas administration apparatus between the point of mixing of the $NO/N_2$ mixture with the oxygen containing gas and inhalation by the patient, in order to keep the concentration of $NO_2$ in said inhalable medicament at less than 5 ppm, ideally less than 1 ppm, in the inhaled gas mixtures because $NO_2$ is a highly toxic gas.

NO gas mixtures are delivered by modified ventilation devices or special modules added to standard ventilators. Such devices are well known and taught, for instance, by U.S. Pat. Nos. 5,558,083; 5,873,359; 5,732,693; and 6,051,241.

Current NO delivery systems are designed for use with ventilators or other breathing gas delivery devices in a hospital or transport setting. Systems to deliver NO to ambulatory patients are in development. The majority of delivery devices are pulsed, sequential, or proportional delivery systems that sense the start of patient inhalation and use one or more electronically controlled valves or switches to deliver a sequenced flow of NO to the patient interface, for example an endotracheal tube, a facemask, or a nasal cannula.

For example, U.S. Pat. No. 6,089,229 discloses a device comprising sensing means for sensing the initiation of an inhalation of a patient and a delivery means responsive to the sensing means.

Further, U.S. Pat. No. 6,142,147 teaches an apparatus with a pressure sensor and a valve controller which is responsive to the pressure sensor, and which selectively connects a first port to a second port, said second port being connected to a source of NO gas, when a negative pressure event is sensed. Here the negative pressure event would be caused by a patient's inhalation so that again a means of sensing the patient's inhalation is used.

Furthermore, U.S. Pat. No. 6,581,599 deals with a method of delivering NO that includes detecting the onset of inspiration.

If adapted for NO delivery to ambulatory patients, such systems suffer from the requirements of a source of electrical power and the need for electromechanical parts to sense and administer sequenced pulses of NO, both of which increase the size of the system, and limit its portability. In addition, due to inevitable lags in timing between detection of the start of patient inhalation and operation of dosing valves, these systems risk delivering their pulses too late in the inhalation, such that a significant fraction of NO is exhaled.

However, there is sufficient evidence to suggest that long term NO therapy may be beneficial for some therapeutic indications, e.g. in treating pulmonary arterial hypertension. For these long term therapies, alternative delivery systems are needed for ambulatory patients. This is comparable to the need for devices for outpatient and in-home oxygen therapy.

For this purpose, a delivery system convenient for use by ambulatory patients, requiring a minimum of electromechanical parts, is required so that they can follow their NO treatment after they have left the hospital setting.

One common patient interface for home oxygen delivery is a standard form nasal cannula. Nasal cannulas are well known and widely used to deliver supplemental oxygen to patients suffering from a wide variety of respiratory and cardiovascular diseases. Generally, one end of an oxygen supply tubing is connected to a source of oxygen, and the other end of the tubing splits into two branches that meet to form a loop, where a set of two nasal prongs are positioned on that loop. The nasal prongs are inserted into a patient's nares, and a constant or time-pulsed flow of oxygen regulated by the source is sent through the tubing and the two branches of the loop so as to exit through the nasal prongs into the patient's nares. During inspiration, the patient inhales oxygen from the prongs together with entrained room air that is drawn through the space between the nasal prongs and the walls of the patient's nares. During exhalation, the patient exhales through the space between the nasal prongs and the walls of the patient's nares, and in the case of a constant oxygen supply flow, oxygen continues to exit into the patient's nares, such that much of this oxygen is carried with the expiratory flow into the surrounding room air. Pulsed oxygen delivery devices attempt to conserve oxygen by sensing the patient's breathing cycle, and then delivering a short-duration flow or pulse of oxygen through a nasal cannula only during inhalation, so as to avoid losing oxygen to the room air during exhalation.

As nasal cannulas are standard in the delivery of supplemental oxygen, many variants exist. For example, U.S. Pat. No. 4,535,767 to Tiep et al. describes an oxygen delivery apparatus consisting of a reservoir cannula, a version of which is available as a commercial product called the Oxymizer from Chad Therapeutics, as described, for example by Dumont and Tiep (Using a reservoir nasal cannula in acute care; *Crit Care Nurse* 2002; 22:41-46). This reservoir cannula includes a chamber in fluid communication with both the oxygen supply line and nasal prongs. The chamber is enclosed in part by a flexible diaphragm that collapses upon inhalation so as to empty its contents through the nasal prongs while at the same time blocking flow from the oxygen supply line to the chamber. The flexible diaphragm then expands during exhalation to fill the chamber with exhaled gas while re-establishing flow from the oxygen supply line into the chamber, such that oxygen from the supply line mixes with and displaces the exhaled gas through the nasal prongs. This type of reservoir cannula has found utility in supplying supplemental oxygen to patients, but is ill-suited for supplying patients with NO/nitrogen gas mixtures in place of oxygen. First, reservoir cannulas as previously described contain means to connect to only a single source of gas; however because commercial NO/nitrogen gas mixtures contain no oxygen, patients may require an additional source of supplemental oxygen. Second, even if air entrained from the room during inhalation provides sufficient oxygen to meet a patient's demand, it is not acceptable that oxygen-containing gas exhaled by the patient mix with NO-containing gas supplied to the chamber. It is well known that NO and oxygen react over time to produce $NO_2$, which is toxic even at relatively low concentrations (e.g. above 5 ppm short term or even 1 ppm for long term), and as such it is well accepted that the residence time during which NO is brought into contact with oxygen should be minimized when supplying these gases to a patient. Finally, the Oxymizer cannula delivers 20 mL of oxygen to the patient each breath. For commonly supplied concentrations of medical NO/nitrogen gas mixtures (e.g. containing 800 ppm NO in balance nitrogen) this delivered volume risks exposing the patient to too high a concentration of NO and too low a concentration of oxygen, especially for younger patients with tidal volumes less than ~200 ml, or for adult patients exhibiting rapid, shallow breathing.

Another nasal cannula variant that exists is commonly referred to as a dual-lumen nasal cannula. For example TeleFlex Hudson RCI Dual Lumen Cannulas are commercially available. These cannulas connect through tubing to a source of oxygen and to a pressure sensing instrument, both of which are in fluid communication with a pair of nasal prongs, the cross section of each prong being split into two sections (or lumen) by a wall, with one section in fluid communication with the source of oxygen, and the other section in fluid communication with the pressure sensing instrument. While it is possible that one could conceive of connecting a source of NO-containing gas in place of the pressure sensing instrument in order to supply both NO and oxygen simultaneously through the dual-lumen cannula, no reservoir, chamber, or other mechanism is included to control the flow of gases. To provide a pulsed delivery of NO, one would need to rely on the systems described above that sense the start of patient inhalation and use one or more electronically controlled valves or switches to deliver a sequenced pulse of NO.

BRIEF SUMMARY OF THE INVENTION

A main goal of the invention is to provide a delivery system convenient for use by ambulatory patients, which allows nitric oxide (NO) to be efficiently administered over extended time periods, i.e. hours, days, weeks, through nasal prongs in a manner that minimizes delivery into the anatomical dead volume at the end of inhalation, and therefore also minimizes exhalation of NO. In so doing, the system must avoid bringing NO-containing gas into contact with oxygen-containing gas until just prior to delivery to the patient, so as to avoid or minimize production of toxic $NO_2$ gas through reaction of NO with oxygen.

Another goal is to provide a delivery system that, in contrast to pulsed delivery systems described in prior art, does not require a sensor to detect the onset of inspiration nor any processing unit (such as a PLC or programmable computer) or other electronics.

A solution according to the present invention concerns a nasal cannula assembly adapted to deliver gases to a patient comprising:
a first compartment and a second compartment separated by a separation wall,
a pair of nasal prongs in fluid communication with the first compartment,
the first compartment comprising a first inlet for introducing a first gas into said first compartment,
the second compartment comprising a second inlet for introducing a second gas into said second compartment, and
the separation wall comprising at least restriction flow element for controlling the passage of gas from the second compartment to the first compartment.

Depending on the embodiment, the nasal cannula assembly according to the present invention can comprise one or several of the following features:
the separation wall comprises at least two valve elements.
the first compartment comprises a first inlet forming a side gases entry in fluid communication with a gas transport conduct.
the nasal cannula assembly further comprises a hollow body comprising an internal chamber comprising at least the first compartment.
at least the first compartment is part of a hollow body forming a gas conduct or a manifold.
said hollow body and said pair of nasal prong are integrally molded from a soft plastics material.
the prongs are detachable from said hollow body to allow different sized prongs to be placed on said hollow body to suit different sized patients.
the restriction flow elements have reentrant apertures for limiting the return flow of gas.
a pair of restriction flow elements is arranged in the separation wall, directly opposite the pair nasal prongs.
the second compartment comprises a deformable wall.
the second compartment forms a deformable-wall reservoir comprising an internal volume for the gas, when fully inflated, of about 0.5 to 5 ml.

The present invention also concerns a breathing assistance apparatus comprising:
a source of NO-containing gas, and
a nasal cannula assembly according to the present invention in fluid communication with said source of NO-containing gas.

Depending on the embodiment, the breathing assistance apparatus according to the present invention can comprise one or several of the following features:
breathing assistance apparatus further comprises a source of an oxygen-containing gas in fluid communication with the nasal cannula assembly.
said source of NO-containing contains NO and nitrogen.
said source of NO-containing contains up to 3000 ppm in volume of NO in a balance of nitrogen.

The present invention also concerns a method for treating pulmonary vasoconstriction in a patient, comprising:
a) providing a nasal cannula assembly according to the present invention, and
b) providing a therapeutically-effective amount of a NO-containing gas to said patient through said nasal cannula assembly for inhalation.

Depending on the embodiment, the nasal cannula assembly according to the present invention can comprise one or several of the following features:
the patient is an adult, an infant or a newborn.
pulmonary vasoconstriction is associated with persistent pulmonary hypertension of the newborn.
pulmonary vasoconstriction is associated with pulmonary arterial hypertension.
the NO-containing gas is mixed with an oxygen-containing gas just before being inhaled by the patient.
the NO-containing gas is a NO/nitrogen mixture.

the NO-containing gas consists in a NO/nitrogen mixture containing up to 3000 ppm by volume of NO.

the $O_2$-containing gas is air or an $O_2/N_2$ mixture containing at least 21 vol. % of $O_2$.

The invention may be further defined in some embodiments by one or more of the following numbered sentences:

1. A nasal cannula assembly (10) adapted to deliver gases to a patient, the nasal cannula assembly (10) comprising:

a) a hollow body (4) configured to be capable of acting as a gas conduct or a gas manifold and comprising an internal chamber (7) defining a first compartment (1), b) the first compartment (1) and a second compartment (2) separated by a separation wall (6), c) a pair of nasal prongs (5) in fluid communication with the first compartment (1), d) the first compartment (1) comprising a first inlet (11) forming a side gases entry in fluid communication with a gas transport conduct and configured to conduct a first gas into said first compartment (1), e) the second compartment (2) having a fully inflated internal volume for a gas of about 0.5 to 5 ml, the second compartment (2) comprising, a second inlet (12) configured to conduct a second gas into said second compartment (2), and a deformable wall (14) forming a part of the boundary between the second compartment (2) and the room atmosphere such that the Compliance of the second compartment (2) is not less than 5 ml/cm $H_2O$ while filling but is less than 0.1 ml/cm $H_2O$ once the second compartment (2) is full, f) the separation wall (6) comprising at least two flow restriction channels (35)

A) having a rounded edge at the entrance from second compartment (2) and

B) having a reentrant aperture at the exit into first compartment (1) and

C) which are oriented and arranged in the separation wall (6) directly opposite the pair nasal prongs (5) to thereby be capable of permitting a passage of gas from the second compartment (2) to the first compartment (1) in a reduced pressure state during an inhalation phase and preventing a majority of flow of the second gas from the second compartment (2) to first compartment (1) in a higher pressure state, during an exhalation phase, relative to the passage of gas during a reduced pressure state, during an inhalation phase, such that during a higher pressure state exhalation phase the majority of flow of the second gas entering the second compartment (2) from the second inlet (12) is retained in the second compartment (2) causing the deformable wall (14) to deform and increase the volume of the second compartment (2) by at least one cubic centimeter in volume or by at least 50% volume, or both, as compared to the second compartment (2) volume at the end of the previous reduced pressure state inhalation phase.

2. A nasal cannula assembly (10) adapted to deliver gases to a patient, the nasal cannula assembly (10) comprising:

a) a first compartment (1) and a second compartment (2) separated by a separation wall (6), b) a pair of nasal prongs (5) in fluid communication with the first compartment (1), c) the first compartment (1) comprising a first inlet (11) configured to conduct a first gas into said first compartment (1), d) the second compartment (2) comprising a second inlet (12) configured to conduct a second gas into said second compartment (2), and e) the separation wall (6) comprising at least one flow restriction channel (35) configured to permit a passage of gas from the second compartment (2) to the first compartment (1) a reduced pressure state during an inhalation phase and prevent a majority of flow of the second gas from the second compartment (2) to first compartment (1) in a higher pressure state, during an exhalation phase, relative to the passage of gas during a reduced pressure state, during an inhalation phase.

3. The nasal cannula assembly according to Sentence 2, wherein the separation wall (6) comprises at least two flow restriction channels (35).

4. The nasal cannula assembly according to Sentence 2 or 3, wherein the first compartment (1) comprises a first inlet (11) forming a side gases entry in fluid communication with a gas transport conduct.

5. The nasal cannula assembly according to Sentence 2, 3 or 4, wherein the nasal cannula assembly further comprises a hollow body (4) comprising an internal chamber (7) comprising at least the first compartment (1).

6. The nasal cannula assembly according to Sentence 2, 3, 4 or 5, wherein at least the first compartment (1) is part of a hollow body (4) configured to be capable of acting as a gas conduct or a gas manifold.

7. The nasal cannula assembly according to Sentence 2, 3, 4, 5, or 6, wherein said hollow body (4) and said pair of nasal prong (5) are integrally molded from a soft plastics material.

8. The nasal cannula assembly according to Sentence 2, 3, 4, 5, 6 or 7, wherein the prongs (5) are detachable from said hollow body (4) and selected from different sized prongs suitable for different sized patient nares.

9. The nasal cannula assembly according to Sentence 3, 4, 5, 6, 7 or 8, wherein the two flow restriction channels (35) connect the first compartment (1) and second compartment (2) and are rounded edged at the entrance from second compartment (2) and have a reentrant aperture at the entrance from the first compartment (1).

10. The nasal cannula assembly according to Sentence 3, 4, 5, 6, 7, 8 or 9, wherein the two flow restriction channels (35) are arranged in the separation wall (6), directly opposite the pair nasal prongs (5).

11. The nasal cannula assembly according to Sentence 2, 3, 4, 5, 6, 7, 8, 9 or 10, wherein the second compartment (2) comprises a deformable wall (14).

12. The nasal cannula assembly according to Sentence 2, 3, 4, 5, 6, 7, 8, 9, 10 or 11, wherein the second compartment (2) forms a deformable-wall reservoir comprising a fully inflated internal volume for the gas of about 0.5 to 5 ml.

13. The nasal cannula assembly according to Sentence 2, 3, 4, 5, 6, 7, 8, 9, 10, 11 or 12, wherein nasal cannula assembly does not comprise a sensor configured to detect an onset of patient inspiration.

14. The nasal cannula assembly according to Sentence 2, 3, 4, 5, 6, 7, 8, 9, 10, 11, 12 or 13, wherein the two flow restriction channels (35) prevent a majority of flow of the second gas from the second compartment (2) to first compartment (1) in a higher pressure state, during an exhalation phase, relative to the passage of gas during a reduced pressure state, during an inhalation phase, optionally further causing the deformable wall (14) to deform and increase the volume of the second compartment (2) by at least one cubic centimeter in volume or by at least 50% volume, or both, as compared to the second compartment (2) volume at the end of the previous reduced pressure state inhalation phase.

15. The nasal cannula assembly according to Sentence 2, 3, 4, 5, 6, 7, 8, 9, 10, 11, 12, 13 or 14, wherein the two flow restriction channels (35) prevent >70% of flow of the second gas from the second compartment (2) to first compartment (1) in a higher pressure state, during an exhalation phase, relative to the passage of gas during a reduced pressure state, during an inhalation phase.

16. The nasal cannula assembly according to Sentence 2, 3, 4, 5, 6, 7, 8, 9, 10, 11, 12, 13, 14 or 15, wherein the two flow restriction channels (35) prevent >90% of flow of the second gas from the second compartment (2) to first compartment (1) in a higher pressure state, during an exhalation phase, relative to the passage of gas during a reduced pressure state, during an inhalation phase.

17. The nasal cannula assembly according to Sentence 11, 12, 13, 14, 15 or 16, wherein the deformable wall (14) of the second compartment (2) has a greater Compliance while filling than when the second compartment (2) is full.

18. The nasal cannula assembly according to Sentence 2, 3, 4, 5, 6, 7, 8, 9, 10, 11, 12, 13, 14, 15, 16 or 17, wherein the nasal prongs (5) includes an external pillow element (8) at an end.

19. The nasal cannula assembly according to Sentence 18, wherein said pillow elements (8) is made of silicone.

20. The nasal cannula assembly according to claim 1, further comprising one or more orifices (13) between the first compartment (1) defining an internal chamber (7) and an external atmosphere.

21. The nasal cannula assembly according to claim 9, wherein a diameter of the two flow restriction channels (35) is between 0.1 mm and 5 mm, and he two flow restriction channels (35) comprise rounded edges at an entrance to the two flow restriction channels (35) designed such that the ratio between a radius of curvature of the rounded edges and the diameters of the two flow restriction channels (35) is greater than 0.02.

22. A breathing assistance apparatus comprising:
    a) a source of NO-containing gas, and
    b) a nasal cannula assembly according to one or more of Numbered Sentence 1, 2, 3, 4, 5, 6, 7, 8, 9, 10, 11, 12, 13, 14, 15, 16, 17, 18, 19, 20, or 21, in fluid communication with said source of NO-containing gas.

23. A breathing assistance apparatus according to Numbered Sentence 22, wherein the breathing apparatus further comprises a source of an oxygen-containing gas in fluid communication with the nasal cannula assembly.

24. A breathing assistance apparatus according to Numbered Sentence 22, wherein said source of NO-containing contains NO and nitrogen.

25. A breathing assistance apparatus according to Numbered Sentence 22, wherein said source of NO-containing contains from 1 ppm to 5000 ppm in volume of NO in a balance of nitrogen.

26. A method for treating pulmonary vasoconstriction in a patient, comprising:
    a) providing a nasal cannula assembly according to one or more of Numbered Sentence 1, 2, 3, 4, 5, 6, 7, 8, 9, 10, 11, 12, 13, 14, 15, 16, 17, 18, 19, 20, or 21, and
    b) providing a therapeutically-effective amount of a NO-containing gas to said patient through said nasal cannula assembly for inhalation to thereby reduce the pulmonary vasoconstriction in the patient.

27. The method according to Numbered Sentence 26, wherein the patient is an adult, an infant or a newborn.

28. The method according to Numbered Sentence 26, wherein pulmonary vasoconstriction is associated with persistent pulmonary hypertension of the newborn.

29. The method according to Numbered Sentence 26, wherein pulmonary vasoconstriction is associated with pulmonary arterial hypertension.

30. The method according to Numbered Sentence 26, wherein the NO-containing gas is mixed with an oxygen-containing gas just before being inhaled by the patient.

31. The method according to Numbered Sentence 26, wherein the NO-containing gas is a NO/nitrogen mixture.

32. The method according to Numbered Sentence 26, wherein the NO-containing gas consists in a NO/nitrogen mixture containing from 1 ppm to 5000 ppmv of NO.

33. The method according to Numbered Sentence 26, wherein the $O_2$-containing gas is air or an $O_2/N_2$ mixture containing at least 21% (by volume) of $O_2$.

BRIEF DESCRIPTION OF THE SEVERAL VIEWS OF THE DRAWINGS

The present invention will be better understood thanks to the following description and explanation made in reference to the Figures, wherein.

[40]—Lung Simulator (ASL 5000; Ingmar Medical)
[22]—22 mm straight connector with sampling port
[30]—Gas sampling line to NO analyzer (Siemens NOA 280i; GE)
[21]—22 mm T piece connector
[23]—22 mm straight connector
[24]—Step-down connector, 22 mm to 4 mm
[35a]—4 mm flow restriction channel; internal to connector [23]
[25]—22 mm straight connector with injection port
[90]—NO injection line
[26]—Breathing filter (ClearGuard II; Intersurgical)

DETAILED DESCRIPTION OF THE INVENTION

Figure 1:
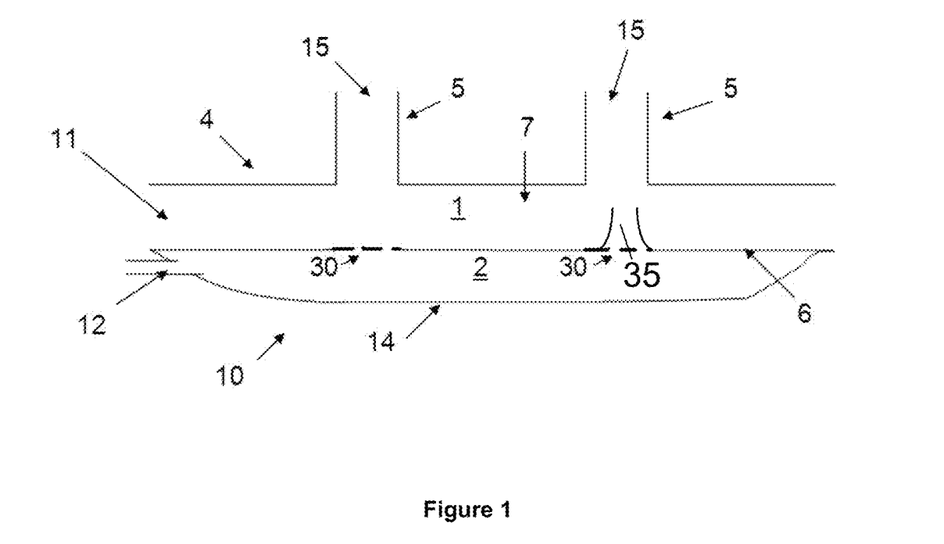
FIG. 1 is a schematic of a first embodiment of a nasal cannula assembly according to the present invention.

A schematic of a first embodiment of the nasal cannula assembly of the present invention is shown in FIG. 1 (in cross section).

The nasal cannula assembly of the present invention is a patient interface generally comprising a pair of nasal prongs 5 coupled indirectly to a deformable-wall 14 having a reservoir 2 supplied with NO contained in nitrogen (12), e.g. at 225, 450, 800 or 1000 ppm in volume.

The pair of nasal prongs 5 is positioned on a hollow body 4, for example an air or oxygen conduit or manifold, comprising an internal hollow volume or chamber 7 thereby forming a first compartment 1 that receives the gases.

The nasal prongs 5 are small conduits or tubes adapted for insertion into the nares of a patient and through which passes the gas mixture that is subsequently inhaled by the patient. Each prong 5 comprises an outlet orifice 15 at its end.

The hollow body 4 can be made of a rigid light material, such as polymer or similar. Preferably, the hollow body 4 and the pair of nasal prong 5 are integrally molded from a soft plastics material. However, the prongs 5 can also be detachable from said hollow body 4 to allow different sized prongs to be placed on said hollow body 4 to suit different sized patients, such as adults and infants. The hollow body 4 is in turn in fluid communication via fluid transfer elements 30, such as flow restriction channel(s), with reservoir 2 formed by the deformable-wall 14 and separation wall 6. In other words, the nasal cannula assembly of the present invention is split into two main inhaled gas compartments 1 and 2 that are separated each from the other by a separation wall 6.

The second compartment 2 forms a deformable reservoir receiving the NO gas through an inlet 12. The deformable wall 14 of the reservoir or second compartment 2 should be made from a thin, flexible sheet of polymer material so that the reservoir readily inflates during exhalation, but collapses, at the start of inhalation. In this manner, NO-containing gas is allowed to accumulate in the reservoir while the patient exhales, and then is released as a bolus at the start of inhalation as the reservoir collapses and its contents empty through the fluid transfer elements 30, such as flow restriction channel(s), into the first compartment 1. Throughout this cycle a constant flow of NO-containing gas may be maintained through the inlet 12.

The second compartment 2 fluidly communicates with the first compartment 1 through one or more fluid transfer elements 30 as shown in FIG. 1. These fluid transfer elements are arranged in the separation wall 6. Preferably, as shown in FIG. 1, two fluid transfer elements 30 are positioned along the conduit 7 forming the hollow main body 4, directly opposite the nasal prongs 5, i.e. each fluid transfer elements 30 is facing one nasal prong 5, so as to facilitate the gas circulation from the second compartment 2 to the first compartment 1 and subsequently to the nasal prongs 5.

The fluid transfer elements 30 are generally one or more flow restriction channel(s) 35 connecting first compartment 1 to second compartment 2 (FIG. 1). The flow restriction channel 35 should be adapted by dimension to limit the majority of flow of NO from second compartment 2 to first compartment 1 (i.e. >50% such as 60, 70 80 or 90%) in the higher pressure state during an exhalation phase relative to the reduced pressure state during an inhalation phase. The flow rate differential between the two pressure conditions may be adjusted by selecting the appropriate flow restriction 35 dimensions (e.g. tubular size), a degree of baffling in the flow restriction channel 35, and/or any other suitable flow restriction elements (e.g. membranes, particle packing, constrictions, etc.). Independent of the specific geometric adaptation, the flow restriction element may be characterized by the equation:

$$\Delta P = 1/2 \rho K V^2,$$

where $\Delta P$ indicates the pressure drop associated with flow of a fluid with density $\rho$ through the flow restriction element at a velocity V representing the mean fluid velocity through the flow restriction element, as averaged, e.g., over the cross-section of the entrance to the element. The coefficient K depends on the geometry and configuration of the flow restriction element, and may thus be used to characterize the flow restriction element, where a larger value of the coefficient K is associated with a larger pressure drop through the flow restriction element for a given fluid density $\rho$ of a fluid traveling at a given mean velocity V. In other words, a larger value of the coefficient K is associated with a lower mean flow velocity V when a given pressure drop $\Delta P$ is imposed across the flow restriction element. Therefore a flow restriction element with larger coefficient K will in general represent a larger barrier to flow through that element.

In light of this understanding, one adaptation of the flow restriction channel 35 connecting first compartment 1 to second compartment 2 is an orifice with dimension selected to produce a coefficient K sufficiently large in value to limit flow from compartment 2 to compartment 1 through the flow restriction channel during the higher pressure state, where the higher pressure in compartment 1 is associated with a small pressure drop $\Delta P$ imposed across the orifice, but at the same time sufficiently small in value to permit flow from compartment 2 to compartment 1 through the flow restriction channel during the reduced pressure state, where the reduced pressure in compartment 1 is associated with a larger pressure drop $\Delta P$ imposed across the orifice. A circular orifice with diameter between around 0.1 mm and around 5 mm, and specifically between 0.5 mm and 2 mm serves as a reasonable solution for many patient breathing patterns. Orifices of different geometry (e.g. an oval, a square, or a slot) but of similar dimension are also reasonable solutions.

Figure 3A:
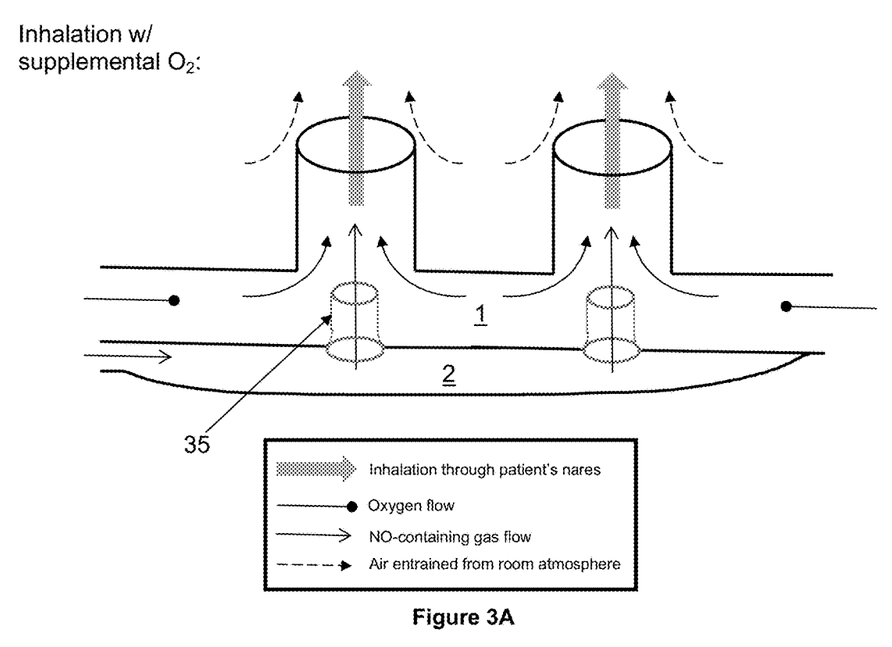
FIGS. 3A-D show a schematic of a second embodiment of a nasal cannula assembly according to the present invention with gas flow illustrated in the inhalation and exhalation phases with supplemental Oxygen (3A-B) and without supplemental Oxygen (3C-D), and FIG. 4 displays an estimated pattern of inhaled NO concentration that could be achieved using a nasal cannula assembly according to the present invention.
Figure 3B:
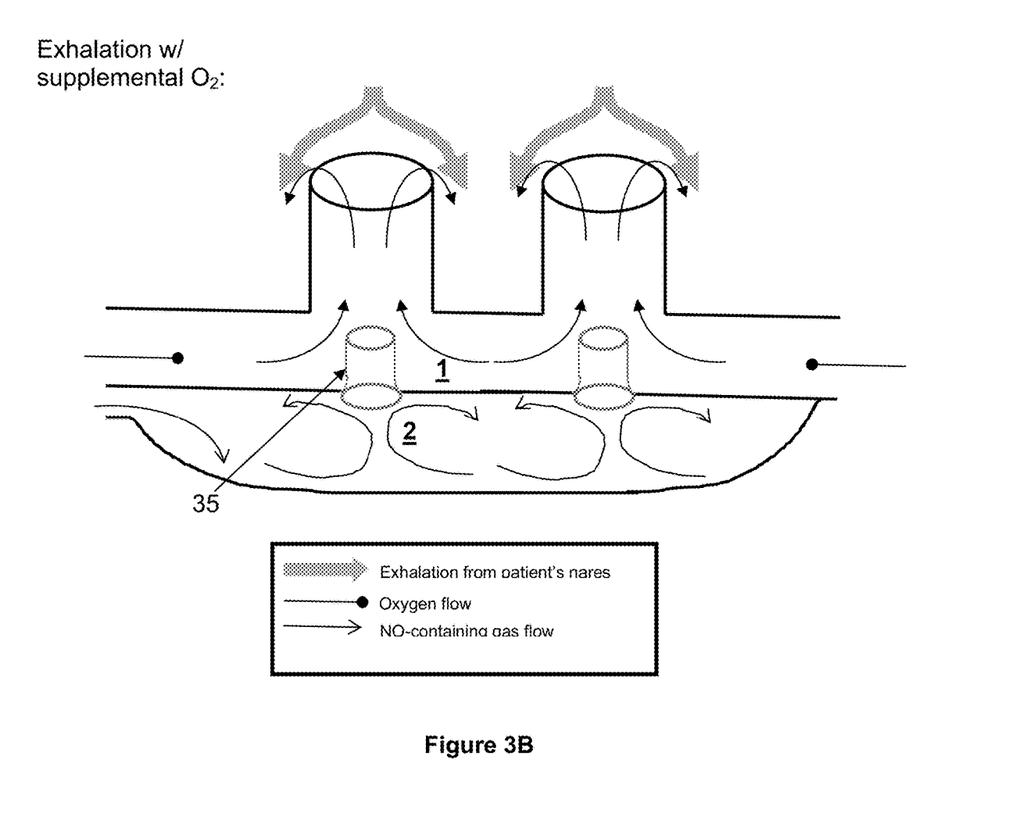
Figure 3C:
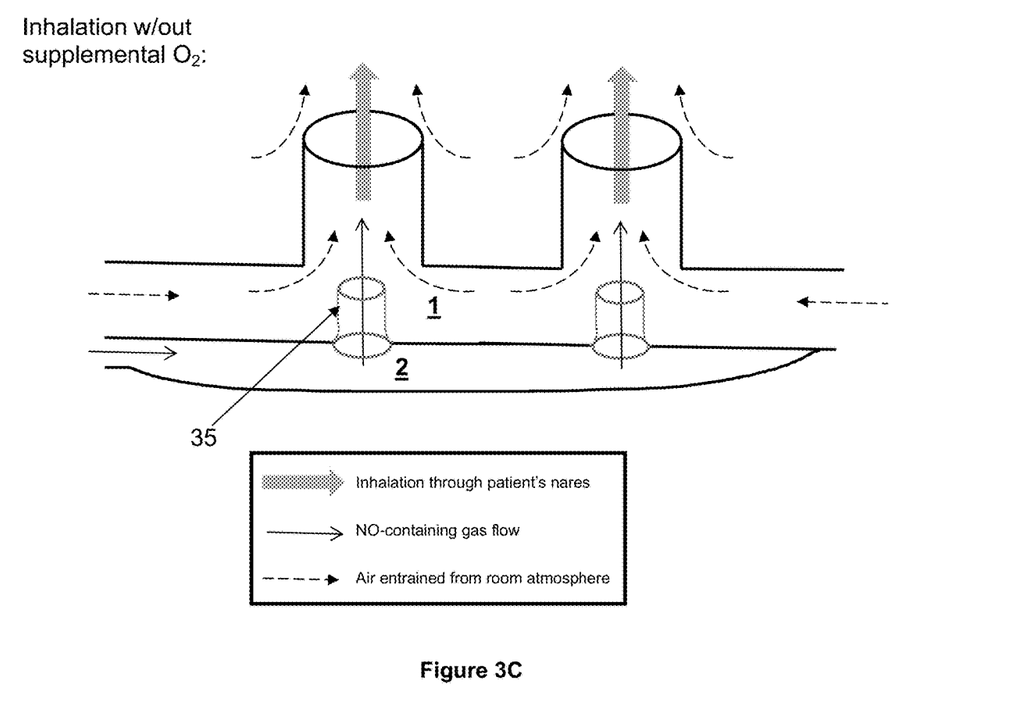
Figure 3D:
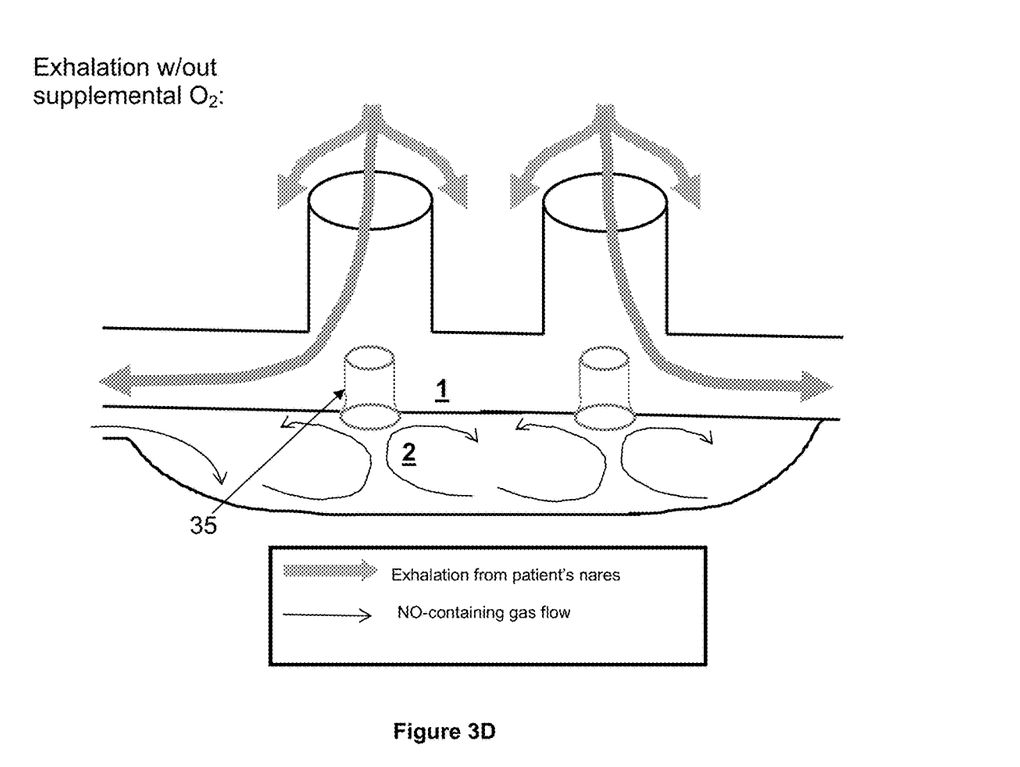

A second adaptation of the flow restriction channel 35 connecting first compartment 1 to second compartment 2 is a constriction channel (FIGS. 3A & 3B) designed such that the constriction channel has a rounded edge at the entrance from compartment 2 for flow in the direction from compartment 2 into compartment 1. Further, the constriction channel protrudes into compartment 1 so as to create a reentrant type entrance for flow in the reverse direction from compartment 1 into compartment 2. It is known that the coefficient K defined above is considerably larger for a reentrant-type entrance than for a rounded-edged entrance, thus in the context of the flow restriction channel discussed here, use of a constriction channel as described above will provide little resistance to flow in the direction from compartment 2 into compartment 1 but will resist flow in the direction from compartment 1 to compartment 2. Accordingly, the constriction channel provides a further advantage for controlling the direction of flow between compartment 1 and compartment 2 in addition to performing the function of modulating flow from compartment 2 to compartment 1 between higher and reduced pressure states as described above for the flow restriction channel in general. The diameter of the constriction channel should generally be between around 0.1 mm and around 5 mm, and specifically between 0.5 mm and 2 mm. The rounded edges at the entrance to the constriction channel should be designed such that the ratio between the radius of curvature of the edge and the diameter of the constriction is greater than 0.02, preferably greater than 0.1; however, increasing this ratio beyond a value of about 0.15 provides little further benefit. For general guidance on restriction flow channel design, see Fox and McDonald, Introduction to Fluid Mechanics, Fifth edition, John Wiley & Sons, N Y, 1998, Chapter 8, or Shaughnessy, Katz, and Schaffer, Introduction to Fluid Mechanics, Oxford University Press, N Y, 2005, Chapter 13.

In any case, the combination of flow restriction channel(s) 35 and deformable wall 14 of the embodiment depicted in FIG. 1 should be responsive to increases and decreases in pressure that develop during exhalation and inhalation, respectively, so as to allow the deformable reservoir 2 to inflate with NO-containing gas during exhalation, and then empty to release this gas through the flow restriction channel(s) 35 into the first compartment 1 during inhalation.

Generally the deformable wall 14 needs to be of a thin, flexible material such that zero or near zero positive pressure above atmospheric develops in compartment 2 as it fills from the Nitric Oxide flow 12 during exhalation (so that flow of gas through the restriction channel(s) 35 remains minimal during exhalation while the bag fills). Reservoir 2 thus should be designed preferably to have infinite or near infinite Compliance (where Compliance=deltaVolume/deltaPressure), while filling—and then drop to zero or near zero Compliance once full.

The first compartment 1 is supplied with an oxygen-containing gas through a first inlet port 11, whereas the second compartment 2 forming a NO-reservoir is supplied with a constant flow of NO-containing gas through a second inlet port 12.

During patient exhalation, the second compartment or reservoir 2 fills with NO containing gas, whereas, during patient inhalation, NO-containing gas mixes with air and/or oxygen in the first compartment 1 as it is inhaled by the patient through the prongs 5.

The volume of the second compartment 2 is configured and sized so as to be small compared to the patient's inhaled tidal volume, so that the second compartment 2 quickly empties during the initial period of the inhalation phase to create a bolus of elevated NO concentration at the start of the inhalation.

Normally high concentrations of NO, e.g. 800 vol. ppm of NO in nitrogen, are delivered to the second compartment 2 from a source of NO/N$_2$, such as a gas cylinder with integrated pressure regulator and flow metering apparatus.

Patient safety is ensured by supplying only low flows of NO-containing gas. For example, to deliver to the patient an amount of NO equivalent to that delivered during continuous supply of gas containing 5 ppmv NO throughout the duration of a 500 ml tidal breath, about 3 ml of gas containing 800 ppmv NO should be supplied each breath.

During tidal breathing, the expiratory time of a typical adult will range from approximately 2 to 5 seconds. Therefore, supply flows on the order of 1 ml/s of NO containing gas are required. In operation, the NO flow rate may be adjusted based on visual inspection of the inflation/deflation of deformable wall 14 to ensure the appropriate flow rate for a specific patient's inhalation pattern. Visual inspection of the inflation/deflation of the deformable wall 14 also provides feedback to the user to ensure proper function of the device, and may be used by a healthcare practitioner in fitting a patient with appropriately sized nasal prongs.

Figure 4:
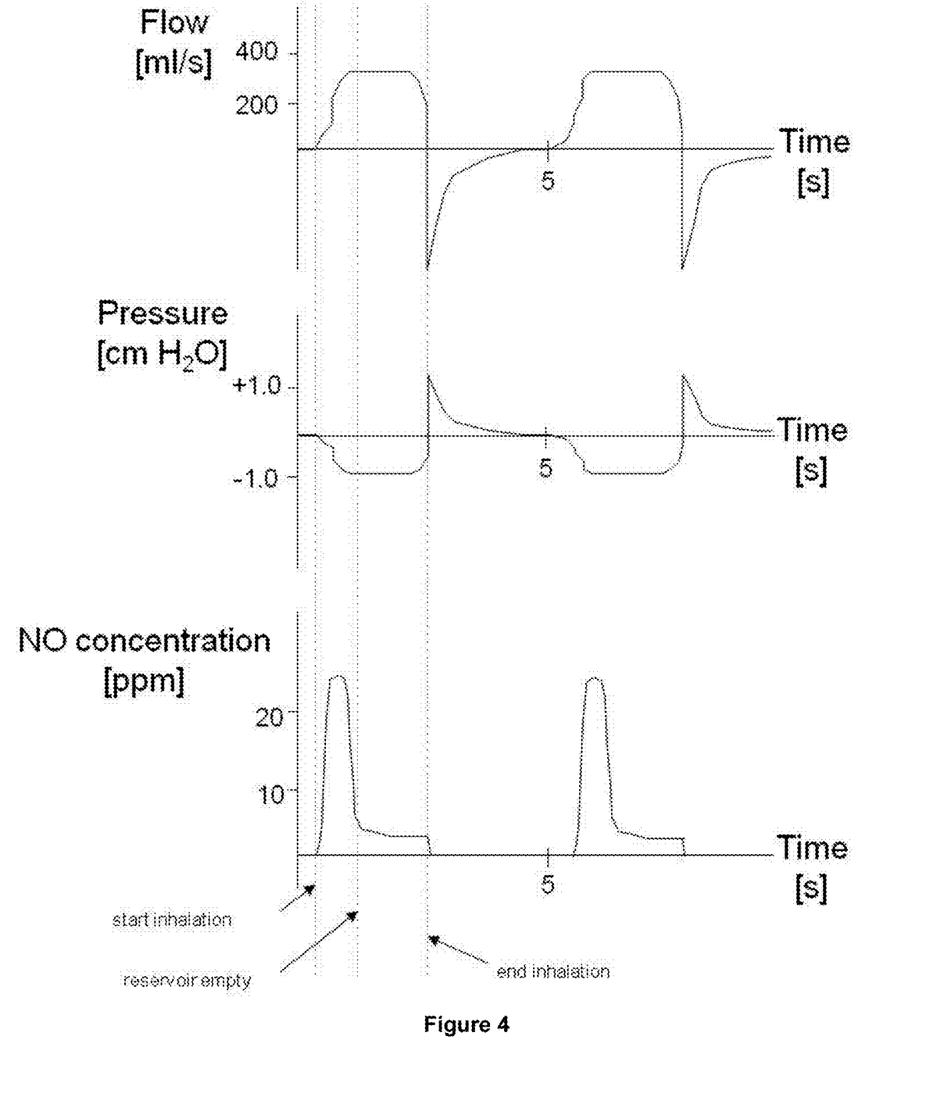

FIG. 4 displays an estimated pattern of inhaled NO concentration that would be achieved using the present invention based on the numbers mentioned above.

More precisely, one can see on FIG. 4 the estimated tidal flow, first compartment 1 pressure, and inhaled NO concentration curves during a typical adult tidal breathing pattern using a nasal cannula assembly 10 according to the present invention supplied with 1 ml/sec flow of gas containing 800 ppmv of NO in N$_2$.

The breathing pattern is shown in the upper curve, with positive flow representing inhalation, and negative flow representing exhalation. The variation of pressure within the first compartment 1 over the breathing cycle is shown in the middle curve. The estimated NO concentration contained in the gas mixture delivered to the patient through the nasal prongs 5 during the inhalation phase of the breathing cycle is shown in the bottom curve.

The NO concentration spikes at the start of inhalation as NO-containing gas is released from the second compartment 2 before rapidly decreasing once the second compartment empties.

Through the later stages of inhalation a low NO concentration is delivered as fresh NO-containing gas supplied through inlet 12 passes into the first chamber 1 and the nasal prongs 5.

In contrast, throughout exhalation, flow of NO-containing gas from the second chamber to the first chamber is prevented or at least reduced by the flow restriction channel(s) 35.

Figure 2:
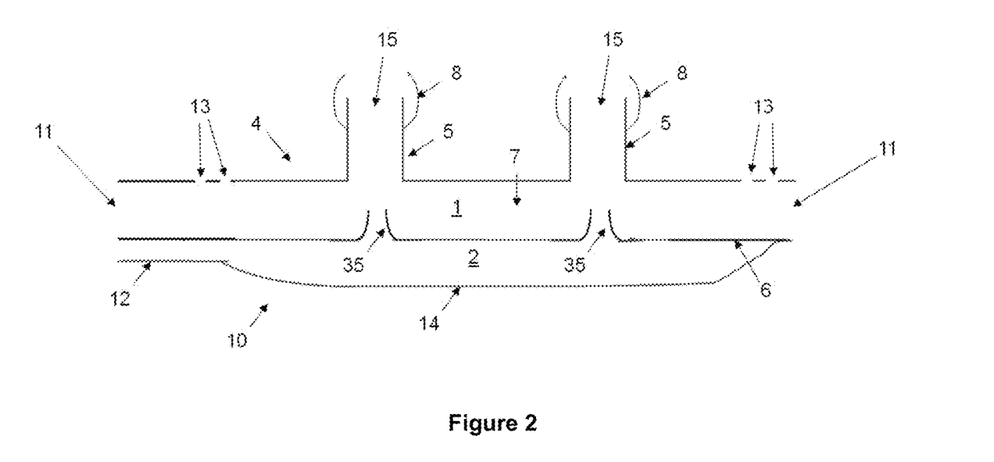
FIG. 2 is a schematic of a second embodiment of a nasal cannula assembly according to the present invention having nasal nare pillows (8) for securing the cannula to the nares.

For some patients, it may be desirable to minimize gas leaks between the nasal prongs 5 and the patient's nares, e.g. to provide continuous positive airway pressure CPAP, Bi-level positive airway pressure (Bi-PAP), or other positive pressure support in combination with NO therapy, or to provide additional control over the higher and reduced pressure states achieved during the breathing cycle. In such circumstances, the nasal cannula assembly 10 may comprise additional elements as shown in FIG. 2.

First, each of the nasal prongs 5 includes an external pillow element 8 at its ends, which is intended to more tightly secure the prongs 5 inside the patient's nares or nostrils. Said pillow elements 8 can be made of soft resilient material, such as silicone or similar.

Second, additional orifices or slots 13 are included between the first compartment 1 defining the internal chamber 7 and the room atmosphere, to allow entrainment of room air, e.g. during inhalation, and exhaust of gases to the room atmosphere, e.g. during exhalation. The number and dimensions of these orifices or slots 13 may be selected so as to achieve a desired range of higher and reduced pressure states during the breathing cycle.

Working Example

Figure 5:
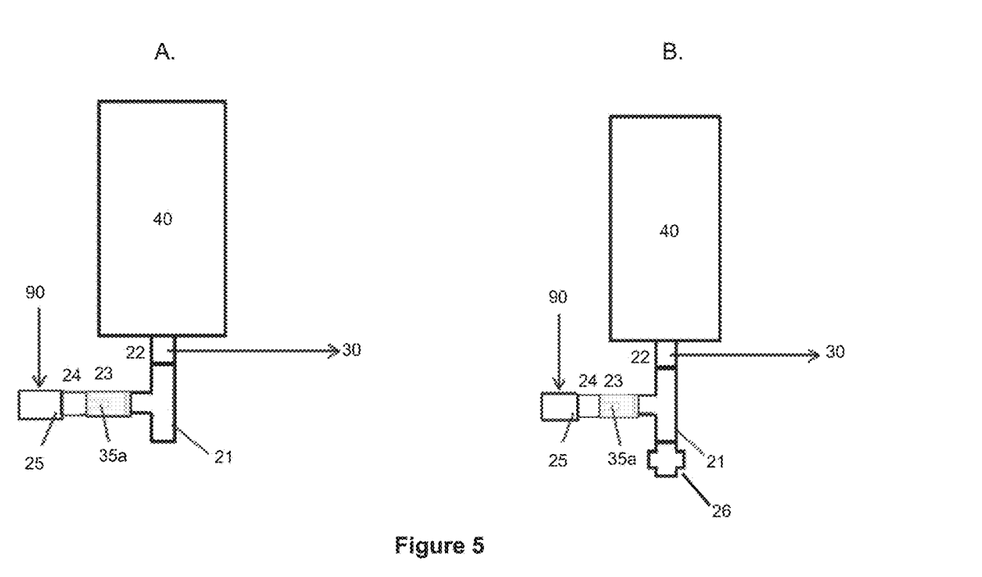
FIG. 5 shows a schematic of a working model for validating restriction flow channel (35) performance under simulated breathing conditions, with elements labeled as follows.
Figure 6:
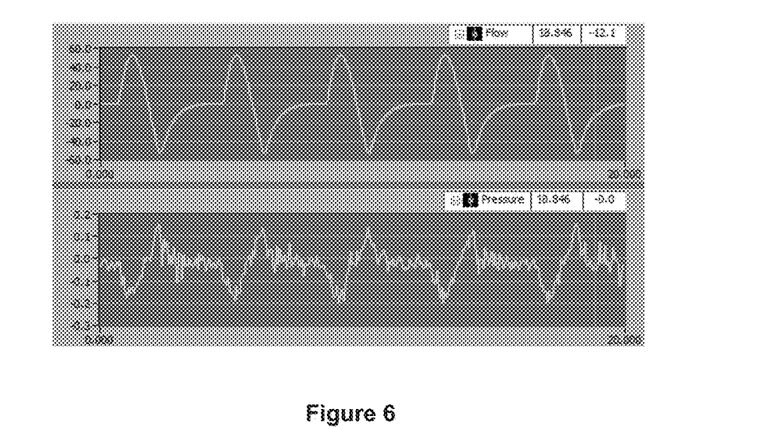
FIG. 6 shows results of an exemplary experiment using the testing apparatus of FIG. 5: Flow (top) and pressure (bottom) versus time waveforms obtained from the lung simulator with no filter. The X-axis units are seconds, while the Y-axis units are L/min and cm H2O, respectively.
Figure 7:
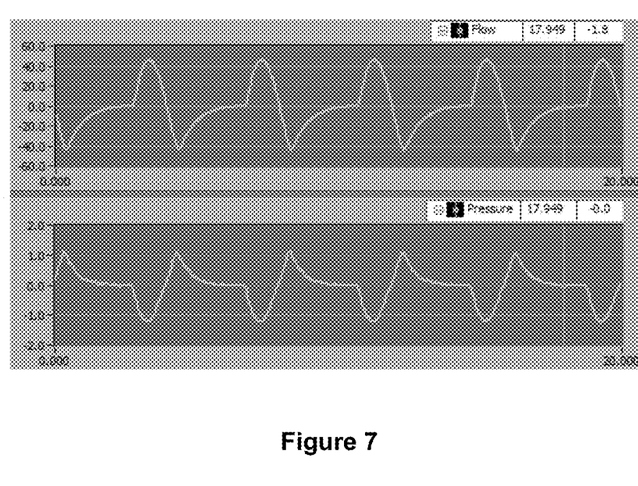
FIG. 7 shows results of an exemplary experiment using the testing apparatus of FIG. 5: Flow (top) and pressure (bottom) versus time waveforms obtained from the lung simulator with the filter in place. The X-axis units are seconds, while the Y-axis units are L/min and cm $H_2O$, respectively.
Figure 8:
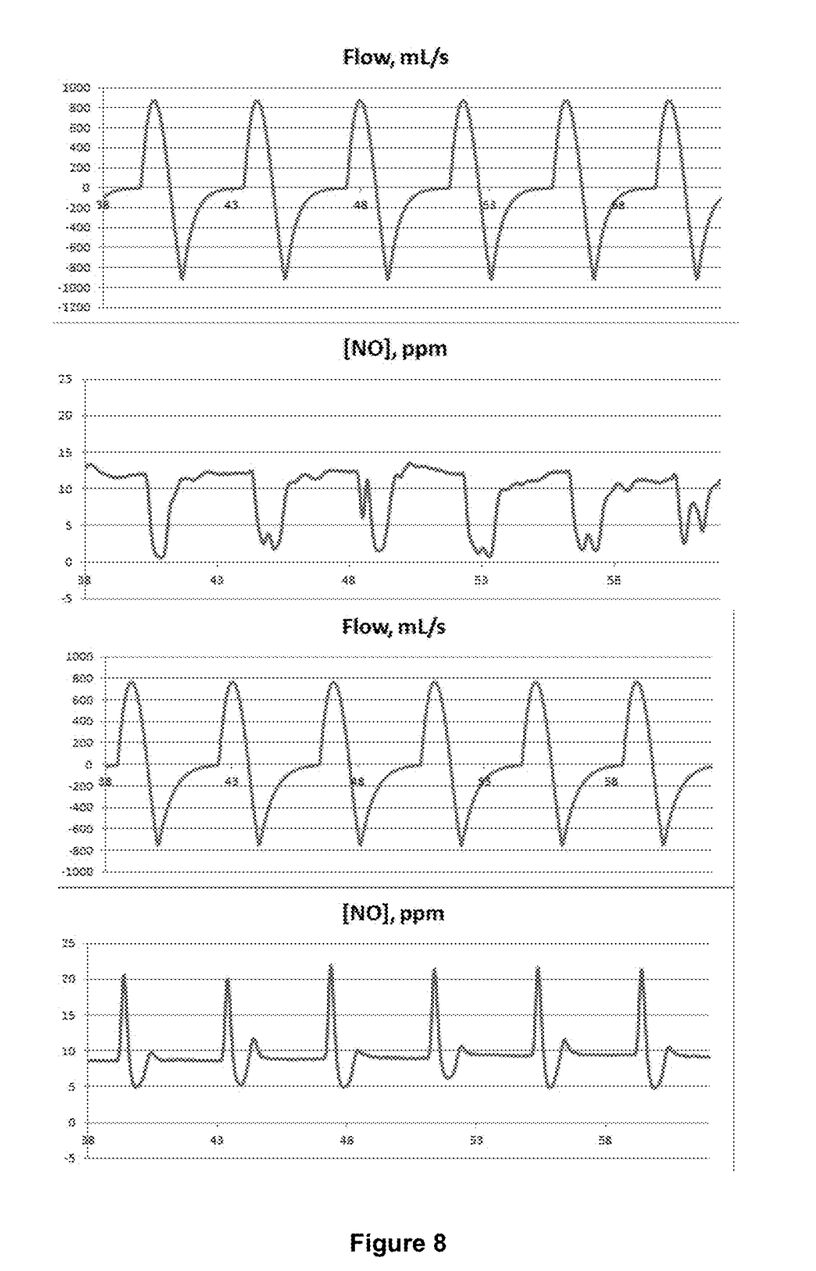
FIG. 8 shows results of an exemplary experiment using the testing apparatus of FIG. 5: Top row: flow versus time waveforms from the lung simulator obtained with no filter (left) and with the filter in place (right). Bottom row: NO concentration versus time waveform as sampled from the first compartment [1] with no filter (left) and with the filter in place (right).

To demonstrate an embodiment of the restriction flow channel of the invention, a mechanical lung simulation device was used to produce a breathing pattern. The breathing pattern was set to that of an average adult human. Breathing patterns representing any patient could be used as the basis for validating a restriction flow channel design for a specific class of patients (e.g. pediatric breathing patterns). The exemplary experiment was performed using a single flow restriction channel [35a] positioned between a first compartment [1] and a second compartment [2]. A 22 mm diameter straight connector [22] including a port for gas sampling via the gas sampling line [30] was positioned between a lung simulator (ASL 5000; Ingmar Medical) [40] and T piece [21]. A second arm of the T piece [21] was connected to a 22 mm straight connector [23], which contained internally a 4 mm flow restriction channel [35a]. The third arm of the T piece [21] was either left open to the room atmosphere, or connected to a breathing filter (ClearGuard II; Intersurgical) [26], which in turn was open to the room atmosphere. The internal conduits of the straight connector with sampling port [22], the T piece [21], and the straight connector [23] formed the first compartment [1]. The flow restriction channel [35a] was connected through a step-down connector [24] to a 22 mm diameter straight connector [25] which included a port for NO gas injection from the NO gas injection line [90]. The opposite end of the straight connector [25] was open to the room atmosphere. The internal conduits of the straight connector with injection port [25] and the step-down connector [24] formed a second compartment [2].

Flow into and out of the lung simulator and the pressure at the entrance to the lung simulator, representing the pressure throughout the first compartment [1], were recorded over time by the lung simulator. The concentration of NO in gas sampled via the gas sampling line [30] was monitored using a chemiluminescence NO analyzer (Siemens NOA 280i; GE). The lung simulator was programmed so as to deliver a 600 mL tidal volume breath at a frequency of 15 breaths/minute, with a sinusoidal inspiratory waveform and a passive, mono-exponential expiratory flow pattern, and an inspiratory time to expiratory time ratio of 2 to 3. A constant flow of 250 mL/min of 800 ppm NO in balance nitrogen gas was delivered through the NO injection line [90]. FIGS. 2 and 3 display flow and pressure versus time waveforms over several breathing cycles for experiments performed without and with the filter [27] in place, respectively. The flow waveform is not appreciably changed between the two experiments, while the pressure waveforms differ. With no filter in place, FIG. 2, the pressure in the first compartment [1] oscillates between a minimum of ~−0.2 cm $H_2O$ during inhalation and a maximum of ~0.1 cm $H_2O$ during exhalation. With the filter [27] in place, FIG. 3, the small added resistance to air flow through the filter results in a reduced pressure state reaching −1.0 cm $H_2O$ during inhalation, and a higher pressure state reaching 1.0 cm $H_2O$ during exhalation.

FIG. 4 again displays flow versus time waveforms (top row) over several breathing cycles for experiments performed without (top left) and with (top right) the filter [27] in place. The bottom row of FIG. 4 displays NO concentrations versus time in gas sampled from the first compartment [1] for experiments performed without (bottom left) and with (bottom right) the filter [27] in place. With no filter in place, that is with pressure states in the first compartment [1] varying between −0.2 cm $H_2O$ during inhalation and 0.1 cm $H_2O$ during exhalation, the NO concentration in gas sampled from the first compartment [1] reached just over 10 ppm during periods of low flow (e.g. at end-expiration), where pressure in the first compartment [1] was near zero, and during inhalation, where pressure in the first compartment [1] was negative, but fell to near zero when expiratory flow rates were appreciable and the pressure in the first compartment [1] rose. With the filter [27] in place, such that the pressure in compartment [1] varied between a reduced pressure state reaching −1.0 cm $H_2O$ during inhalation, and a higher pressure state reaching 1.0 cm $H_2O$ during exhalation, the variation in delivered NO concentration was magnified: a bolus of gas containing NO concentration as high as 20 ppm passed through the first compartment [1] during inhalation, and the NO concentration fell to approximately 5 ppm during periods where expiratory flow was appreciable, such that the higher pressure state was achieved in the first compartment [1], before rising to 10 ppm through the remainder of the breathing cycle.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

The invention claimed is:

1. A nasal cannula assembly (10) adapted to deliver gases to a patient, the nasal cannula assembly (10) comprising:
   a) a hollow body (4) configured to be capable of acting as a gas conduct or a gas manifold and comprising an internal chamber (7) defining a first compartment (1),
   b) the first compartment (1) and a second compartment (2) separated by a separation wall (6),
   c) a pair of nasal prongs (5) in fluid communication with the first compartment (1),
   d) the first compartment (1) comprising a first inlet (11) forming a side gases entry in fluid communication with a gas transport conduct and configured to conduct a first gas into said first compartment (1),
   e) the second compartment (2) having a fully inflated internal volume for a gas of about 0.5 to 5 ml, the second compartment (2) comprising,
      a second inlet (12) configured to conduct a second gas into said second compartment (2), and
      a deformable wall (14) forming a part of a boundary between the second compartment (2) and a room atmosphere such that the compliance of the second compartment (2) is not less than 5 ml/cm $H_2O$ while filling but is less than 0.1 ml/cm $H_2O$ once the second compartment (2) is full, f) the separation wall (6) comprising two flow restriction channels (35)

A) having a rounded edge at an entrance from the second compartment (2) and

B) having a reentrant aperture at an exit into the first compartment (1) and C) which are oriented and arranged in the separation wall (6) directly opposite the pair of nasal prongs (5) to thereby be capable of permitting a passage of gas from the second compartment (2) to the first compartment (1) in a reduced pressure state during an inhalation phase and preventing a majority of flow of the second gas from the second compartment (2) to the first compartment (1) in a higher pressure state, during an exhalation phase, relative to the passage of gas during the reduced pressure state, during an inhalation phase, such that during the higher pressure state exhalation phase the majority of flow of the second gas entering the second compartment (2) from the second inlet (12) is retained in the second compartment (2) causing the deformable wall (14) to deform and increase the internal volume of the second compartment (2) by at least 50% volume, as compared to the second compartment (2) volume at the end of the previous reduced pressure state inhalation phase.

2. The nasal cannula assembly according to claim 1, further comprising one or more orifices (13) in the first compartment (1) defining a fluid communication from an internal chamber (7) to an external atmosphere.

* * * * *